United States Patent
Satzger et al.

(10) Patent No.: US 9,952,236 B2
(45) Date of Patent: Apr. 24, 2018

(54) METHOD AND DEVICE FOR PROCESS MONITORING

(75) Inventors: Wilhelm Satzger, Munich (DE); Siegfried Sikorski, Munich (DE); Karl-Heinz Dusel, Unterschleissheim (DE); Wilhelm Meir, Gablingen (DE); Bertram Kopperger, Dachau (DE); Josef Waermann, Viehbach (DE); Andreas Jakimov, Munich (DE); Manuel Hertter, Munich (DE); Hans-Christian Melzer, Jetzendorf (DE); Thomas Hess, Munich (DE)

(73) Assignee: MTU AERO ENGINES AG, Munich (DE)

( * ) Notice: Subject to any disclaimer, the term of this patent is extended or adjusted under 35 U.S.C. 154(b) by 1157 days.

(21) Appl. No.: 13/981,186

(22) PCT Filed: Jan. 11, 2012

(86) PCT No.: PCT/DE2012/000020
§ 371 (c)(1),
(2), (4) Date: Jul. 24, 2013

(87) PCT Pub. No.: WO2012/100766
PCT Pub. Date: Aug. 2, 2012

(65) Prior Publication Data
US 2013/0343947 A1 Dec. 26, 2013

(30) Foreign Application Priority Data
Jan. 28, 2011 (DE) .................. 10 2011 009 624

(51) Int. Cl.
| | | |
|---|---|---|
| G01N 35/00 | (2006.01) | |
| B22F 3/105 | (2006.01) | |
| B29C 67/00 | (2017.01) | |
| B33Y 40/00 | (2015.01) | |
| G01N 25/72 | (2006.01) | |

(52) U.S. Cl.
CPC .............. G01N 35/00 (2013.01); B22F 3/105 (2013.01); B22F 3/1055 (2013.01); B29C 67/0077 (2013.01); B29C 67/0085 (2013.01); B29C 67/0088 (2013.01); B22F 2003/1056 (2013.01); B22F 2003/1057 (2013.01); B33Y 40/00 (2014.12); G01N 25/72 (2013.01); Y02P 10/295 (2015.11)

(58) Field of Classification Search
CPC ...... B22F 2003/1056; B22F 2003/1057; B22F 3/105; B22F 3/1055; B29C 67/0077; B29C 67/0085; B29C 67/0088; G01N 25/72; G01N 35/00; Y02P 10/295
USPC .............. 702/136, 155, 159, 172, 182, 183; 219/121.63, 121, 66, 83; 250/559.2; 264/40.1; 356/237.2; 700/123; 382/152
See application file for complete search history.

(56) References Cited

U.S. PATENT DOCUMENTS

| | | | |
|---|---|---|---|
| 6,046,426 A | 4/2000 | Jeantette et al. | |
| 6,122,564 A | 9/2000 | Koch et al. | |
| 6,215,093 B1 | 4/2001 | Meiners et al. | |
| 6,492,651 B2 | 12/2002 | Kerekes | |
| 6,580,959 B1 | 6/2003 | Mazumder | |
| 6,630,995 B1 * | 10/2003 | Hunter | G01N 21/94 356/237.2 |
| 6,694,284 B1 * | 2/2004 | Nikoonahad | G01N 21/211 702/155 |
| 7,003,864 B2 | 2/2006 | Dirscherl | |
| 2002/0104973 A1 | 8/2002 | Kerekes | |
| 2004/0099983 A1 | 5/2004 | Dirscherl | |
| 2004/0200816 A1 | 10/2004 | Chung et al. | |
| 2007/0176312 A1 | 8/2007 | Clark et al. | |
| 2007/0217672 A1 * | 9/2007 | Shannon | G06T 7/0006 382/152 |
| 2009/0206065 A1 | 8/2009 | Kruth et al. | |

FOREIGN PATENT DOCUMENTS

| | | |
|---|---|---|
| DE | 19649865 C1 | 2/1998 |
| DE | 10058748 C1 | 7/2002 |
| DE | 102004017769 A1 | 12/2004 |
| EP | 1815936 A1 | 8/2007 |

OTHER PUBLICATIONS

Siemens "Kooperationsforum „Generative Fertigungstechnologien Generative Verfahren Einsatz und Forschung", Apr. 29, 2009, 5 pgs.
Hanser "Avantgardistische Kreationen in Titan gesintert", Rapid X Branche, Jan. 2010, 52 pgs.

* cited by examiner

*Primary Examiner* — John H Le
(74) *Attorney, Agent, or Firm* — Abel Law Group, LLP

(57) ABSTRACT

Disclosed is a method for monitoring a generative fabrication process in which a component is formed in an installation space from a multiplicity of layers by using a three-dimensional data model and a following layer is fixed to a preceding layer by means of a high-energy beam. The method comprises detecting the component at least optically and detecting the installation space thermally during layer application. Also disclosed is a device for carrying out the method.

12 Claims, No Drawings

METHOD AND DEVICE FOR PROCESS MONITORING

BACKGROUND OF THE INVENTION

1. Field of the Invention

The invention relates to a method for monitoring a generative fabrication process and to a device for carrying out such a method.

2. Discussion of Background Information

A method and a device for the generative production of a component are shown, for example, in German patent DE 196 49 865 C1. The component is built up in an installation space from a multiplicity of individual powder layers. Here, a laser beam is guided over a layer to be produced in accordance with a cross-sectional geometry of a three-dimensional data model, said layer then being fixed to a preceding powder layer. Generative production is suitable in particular for producing components having complex geometries but checking of the component properties has hitherto been carried out only after the component production, as a result of which comparatively high costs arise for quality assurance measures.

In recent times, however, it has increasingly been possible to observe a trend to monitor the generative fabrication process directly and continuously. Thus, for example, in DE 100 58 748 C1, monitoring of the production process by using optical and thermal sensors is proposed. In the periodical "rapidX", periodical for additive fabrication, Carl Hanser Verlag, Munich, Edition 1-2010, in the article "Fertig zum Abheben" [Ready to go], direct and continuous monitoring of a generative fabrication process is likewise mentioned. In the contribution "Generative Verfahren Einsatz and Forschung" [Generative process use and research] dated Apr. 29, 2009 to the cooperation forum "Generative Fertigungstechnologien" [Generative fabrication technologies] under the slide-show heading "Schritte zur Qualifizierung des SLM-Prozesses" [Steps toward qualification of the SLM process], process monitoring by means of optical systems is mentioned. According to this prior art, direct and continuous monitoring of a generative fabrication process such as selective laser sintering (SLS) or selective laser melting (SLM) appear to be known per se, but no specification of the respective monitoring process is given.

The invention is based on the object of presenting a method for monitoring a generative fabrication process which permits direct and continuous process monitoring, and also of devising a device for carrying out such a method.

SUMMARY OF THE INVENTION

In a method according to the invention for monitoring a generative fabrication process, in which a component is formed in an installation space from a multiplicity of layers by using a three-dimensional data model and a following layer is fixed to a preceding layer by means of a high-energy beam, according to the invention the component is detected at least optically and the installation space thermally during layer application. The solution according to the invention permits direct and continuous and thus online and real-time process monitoring, by which means information about each produced layer of the component is acquired. As a result of the at least optical monitoring of the respective layer or the respective layer section in combination with the thermal monitoring of the installation space, interactions between the component and the installation space can be detected. At the end of the fabrication process, a detailed statement about the condition and the properties of the fabricated component and thus about the quality thereof can be made. Subsequent operations for quality assurance are thus rendered superfluous. Costs for the subsequent quality assurance are completely eliminated. The information about the component is available seamlessly, so that the quality of each individual layer or of each individual layer section is detected.

In a preferred exemplary embodiment, the data acquired during the fabrication process is assessed and, in the event of a respective maximum permissible deviation being exceeded, process parameters are changed appropriately. In this way, the running production process is readjusted in real time, which means that the component can be produced with optimal quality. This thus rules out, for example, bonding defects propagating over the entire component.

Preferably, outline detection or optical 2-D measurement is carried out after the last produced layer and/or after the application of a powder. In this way, individual distortion of each layer can be detected and the respective beam guidance can be adapted appropriately during the following layer. The outline detection can be carried out, for example, within the context of 2-D image processing.

If the 2-D examination is carried out after the application of the powder but before the sintering or fusing, pores can be detected and eliminated.

Alternatively or additionally, a color analysis of the last produced layer can be carried out, by which means, for example, foreign particles can be detected.

In one process variant, the last fabricated layer is examined with regard to the nature and properties thereof such as bonding defects, layer thickness and foreign particles. This can be carried out, for example, by means of a thermal analysis based on methods and means from thermography. If the thermographic examination is carried out after the application of the powder but before the sintering or fusing, then foreign particles can be detected. If foreign particles are present, then the powder layer can simply be removed.

Detecting the nature of the respective layer can also be carried out or in addition to the thermal analysis, by means of light reflected from the layer. This can be carried out, for example, by means of a light source for emitting light waves and by using a light sensor to detect the reflected light.

The nature of the last produced layer can also be detected by means of eddy currents. This can be done, for example, by means of eddy current sensors and is suitable in particular in the case of flat layers.

In one exemplary embodiment, a melt bath produced by the high-energy beam is detected thermally, so that it is possible to monitor whether the high-energy beam has been set optimally with regard to the parameters thereof such as power, beam diameter, feed rate. This thermal monitoring can be carried out, for example, by following the temperature of the melt bath at the point of impingement of the energy beam with the aid of a tracking pyrometer.

In one exemplary embodiment, the component is detected with respect to the entire distortion thereof after its production. This can be carried out via an optical 3-D measurement of the fabricated component within the context of 3-D image processing.

One method variant permits classification of layer material in real time, on the basis of which process parameters are then adjusted or parameter control is carried out. When a powder is used as layer material, fluctuations in the powder quality during the fabrication process can thus be compensated for by means of adapted process parameters.

In one exemplary embodiment of the instant method, the roughness is determined after a layer has been produced and/or after application of the powder.

Carrying out such a method in accordance with the invention involves at least one optical detection device for the optical detection of at least one component layer and at least one thermal detection device for the thermal detection of an installation space accommodating the component. A device of this type permits direct and continuous monitoring of all the component layers and control and regulation of process parameters.

Other advantageous exemplary embodiments of the invention are the subject matter of further subclaims.

DETAILED DESCRIPTION OF THE INVENTION

In a preferred method according to the invention, a component is formed in an installation space layer by layer from a multiplicity of layers, preferably from a powder material. A high-energy beam such as a laser or electron beam is guided over a layer to be solidified in accordance with the cross-sectional geometry of a three-dimensional data model, said layer being fixed to the preceding layer during solidification. During the impingement of the high-energy beam, a melt bath is formed and the layer to be solidified is partially melted. After the high-energy beam has been led onward, the molten layer section cools down and is fixed to a preceding layer section or the preceding layer. The layer lying underneath is at least partly re-melted; a continuous welded connection is produced.

In order to monitor the fabrication process, the component is detected optically and thermally and the installation space thermally during layer application. Optical detection can be carried out, for example, by means of an optical camera, the recorded image from which is then superimposed on a reference image of the last produced layer for the purpose of evaluation. Thermal detection can be carried out, for example, by means of a thermal imaging camera, via which the heat radiation emitted from the installation space is detected in the infrared range, said radiation being determined substantially by the component or component section positioned in the installation space and the high-energy beam. The actual data acquired relating to the condition of the applied component layer and the installation space is compared with stored reference data. In the event of a respective maximum permissible deviation being exceeded, an active intervention in the process control is made and process parameters are changed appropriately. Thus, for example, in the event of an excessively high temperature gradient within the component, the layer application, the high-energy beam with respect to the parameters thereof such as output, beam diameter and feed rate can be changed appropriately. Likewise, pre-heating of the powder to a specific temperature for the application can be matched to the actual data determined. Furthermore, in order to adjust the process parameters, the quality of the powder itself can be detected and evaluated.

Preferably, 2-D image processing of the last produced layer is carried out in order to detect the outlines thereof. In the event of a layer distortion outside predefined tolerance limits being determined, at least the guidance of the high-energy beam is adapted appropriately.

In addition, thermal analysis of the last produced layer is carried out, for example with the aid of thermography, in order to measure the respective layer properties such as bonding defects within the layer, bonding defects to the preceding layer, layer thickness and foreign particles incorporated in the layer. Furthermore, the last produced layer is irradiated with light and the reflected light is detected continuously and evaluated in order to determine foreign particles and processing defects. If the last produced layer is a flat layer, the nature thereof or the structure thereof is additionally detected by means of eddy currents and evaluated appropriately.

After the production of the component, an optical 3-D measurement is carried out. Here, in order to detect component distortion, the external geometry thereof is measured in its entirety.

In addition, during the fabrication process, the temperature of the melt bath during the impingement of the high-energy beam on the respective layer is observed with the aid of a pyrometer tracking the high-energy beam.

A device according to the invention for carrying out such process monitoring has at least one optical detection device such as an optical camera for detecting a component layer or the entire component and also a thermal detection device such as a thermal imaging camera for the thermal detection of the installation space. Furthermore, the device has a pyrometer tracking the high-energy beam, a light measuring device having a light source for emitting light waves in the direction of the last produced layer and having a light sensor for detecting the reflected light, and also an eddy current sensor for detecting the respective layer structure.

Disclosed is a method for monitoring a generative fabrication process in real time, wherein a component is detected at least optically and the installation space thermally during layer application, and also a device for carrying out such a method.

What is claimed is:

1. A generative fabrication process of a component, wherein the process comprises forming the component in an installation space from a multiplicity of layers by using a three-dimensional data model and fixing a following layer to a preceding layer by means of a high-energy beam, and wherein the process further comprises (i) carrying out an optical 3-D measurement of the component at least one of after a layer has been produced and after application of a powder, and (ii) carrying out thermography after application but before sintering or fusing of a powder.

2. The process of claim 1, wherein data acquired during the fabrication process is assessed and, in the event of a maximum permissible deviation being exceeded, process parameters are changed.

3. The process of claim 1, wherein at least one of after a layer has been produced and after application of a powder a 2-D measurement is carried out.

4. The process of claim 1, wherein a color analysis of a last produced layer is carried out.

5. The process of claim 1, wherein light reflected from a last produced layer is detected.

6. The process of claim 1, wherein a nature of a produced layer is detected by means of eddy currents.

7. The process of claim 1, wherein a melt bath produced by the high-energy beam is detected thermally.

8. The process of claim 7, wherein a pyrometer for tracking the high-energy beam is used.

9. The process of claim 1, wherein a classification of layer material is carried out and, based on a result thereof, a control of process parameters is carried out.

10. The process of claim 1, wherein at least one of after a layer has been produced and after application of a powder a roughness is determined via a laser profiling method.

11. A device for carrying out the process of claim 1, wherein the device comprises (a) at least one optical detection device for optical detection of at least one component layer by 3-D imaging and (b) at least one thermal detection device for detection by thermography of an installation space that accommodates the component.

12. The device of claim 11, wherein the device further comprises at least one of a pyrometer for tracking the high-energy beam and an eddy current sensor for detecting a layer structure.

* * * * *